(12) United States Patent
Brossel

(10) Patent No.: US 10,449,160 B2
(45) Date of Patent: Oct. 22, 2019

(54) SYSTEM GENERATING A CONSTRAINT FIELD, AND MEDICAL DEVICE IMPLEMENTING THE SAME

(71) Applicant: Remy Brossel, Raphele les Arles (FR)

(72) Inventor: Remy Brossel, Raphele les Arles (FR)

(73) Assignee: CELL CONSTRAINT & CANCER (CC&C), Raphèle-les-Arles (FR)

( * ) Notice: Subject to any disclaimer, the term of this patent is extended or adjusted under 35 U.S.C. 154(b) by 364 days.

(21) Appl. No.: 14/904,580

(22) PCT Filed: Jul. 11, 2014

(86) PCT No.: PCT/EP2014/064995
§ 371 (c)(1),
(2) Date: Jan. 12, 2016

(87) PCT Pub. No.: WO2015/004285
PCT Pub. Date: Jan. 15, 2015

(65) Prior Publication Data
US 2016/0143859 A1 May 26, 2016

(30) Foreign Application Priority Data

Jul. 12, 2013 (EP) .................................... 13176364

(51) Int. Cl.
*A61K 9/50* (2006.01)
*A61N 2/00* (2006.01)
(Continued)

(52) U.S. Cl.
CPC .......... *A61K 9/5094* (2013.01); *A61K 9/5115* (2013.01); *A61K 41/00* (2013.01); *A61N 1/406* (2013.01); *A61N 2/004* (2013.01)

(58) Field of Classification Search
CPC .... A61K 9/5094; A61K 9/5115; A61K 41/00; A61N 2/004; A61N 1/406
See application file for complete search history.

(56) References Cited

U.S. PATENT DOCUMENTS

| 6,514,481 | B1 * | 2/2003 | Prasad | .................... | A61N 1/406 |
|           |      |        |        |                      | 324/307    |
| 2006/0147381 | A1 * | 7/2006 | Jones | ..................... | A61N 1/406 |
|           |      |        |        |                      | 424/9.323  |

(Continued)

FOREIGN PATENT DOCUMENTS

| EP | 2 508 171 A1 | 10/2012 |
| JP | 2009114066 | 5/2009 |

(Continued)

OTHER PUBLICATIONS

International Search Report, dated Sep. 17, 2014, from corresponding PCT application.

*Primary Examiner* — Kaylee R Wilson
(74) *Attorney, Agent, or Firm* — Young & Thompson

(57) ABSTRACT

Disclosed is a system including (1) an injection device including injectable magnetizable nanoparticles and a component for injecting the same, and (2) a unit for applying a constraint physically and/or mechanically to a tumor associated to an neoangiogenic network where, after having been injected, the particles are retained. Also disclosed is a method for treating tumors, especially tumors associated with a neoangiogenic network, including the steps of: injecting a composition including magnetizable nanoparticles; optionally performing imaging using an imaging device to detect a concentration of nanoparticles retained in the neoangiogenic network; and applying a contact-free constraint onto a tumor in vivo, by a gradient of magnetic field and the application being directed to the tumor region.

20 Claims, 11 Drawing Sheets

(51) Int. Cl.
*A61N 1/40* (2006.01)
*A61K 41/00* (2006.01)
*A61K 9/51* (2006.01)

(56) References Cited

U.S. PATENT DOCUMENTS

| | | |
|---|---|---|
| 2010/0040555 A1 | 2/2010 | Levy et al. |
| 2011/0054237 A1* | 3/2011 | Shapiro ............... A61B 5/411 |
| | | 600/12 |
| 2011/0223255 A1 | 9/2011 | Thiesen et al. |

FOREIGN PATENT DOCUMENTS

| | | |
|---|---|---|
| JP | 2009534350 | 9/2009 |
| WO | 2007/118884 | 10/2007 |
| WO | 2008/132214 A1 | 11/2008 |

* cited by examiner

SYSTEM GENERATING A CONSTRAINT FIELD, AND MEDICAL DEVICE IMPLEMENTING THE SAME

FIELD OF INVENTION

The present invention pertains to the field of physical sciences. More especially, this invention relates to a system comprising nanoparticles and means to remotely apply a gradient of magnetic field on a tumor region. According to the invention, nanoparticles are injected intravenously in a subject having a tumor. Nanoparticles are injected and after migration, are located at the tumor region. Application of a gradient of magnetic field in the tumor region where the nanoparticles are located, results in the generation of a constraint field on the tumor surroundings allowing the reduction of the volume and histological surfaces of the tumor.

BACKGROUND OF INVENTION

Using implantable nanoparticles in medicine is well-known, and a number of references use nanoparticles for magnetic targeting of drugs. For example EP 2508171 mentions the use of nanoparticles for guiding and accumulating to a target tissue a pharmaceutical composition coated onto said nanoparticles. US 2011223255 (MagForce) describes implantable products containing nanoparticles and their use in medicine, particularly for thermotherapeutic after-treatment, after surgical removal of tumors.

In the treatment of cancer, there is an evident need for new medicinal—and particularly physical—strategies for treating tumors: novel cancer treatment therapies using alternating electric field were attempted to disturb the rapid cell division exhibited by cancer cells. One system was developed by Novocure company and was approved by the US FDA on Apr. 15, 2011 for the treatment of recurrent Glioblastoma Multiforme, a type of malignant brain tumor.

SUMMARY

This invention proposes a new medical system and method for the treatment of tumors, implementing an injection device comprising injectable magnetizable nanoparticles and a magnetic field gradient for generating a constraint field onto tumor surroundings, and optionally comprising magnets. The method of this invention involves the injection, in a subject in need thereof, of a number of magnetizable nanoparticles and the application of an external gradient of magnetic field in the tumor region where the nanoparticles are retained.

The Applicant observed that, when the nanoparticles are injected intravenously, they are retained by the neoangiogenic network. It was observed that the randomized distribution of the injected nanoparticles in the neoangiogenic network surrounding the tumor surprisingly formed some kind of a hollow and discontinuous sphere. The tumor is thus located within said sphere.

This configuration of injected nanoparticles in the neoangiogenic network surrounding the tumor, creates conditions such that, when a gradient of magnetic field is applied onto the tumor region, a consequence of this application is the generation of a constraint field, and further of a constraint which is applied on the cells; this constraint leads to a change of the phenotype of the tumor cell to a normal or partially normal cell phenotype. Especially, this physical and/or mechanical constraint allows reducing the volume of a tumor and acts on the two histological surfaces of the tumor exposed to the external gradient of magnetic field.

In other words, the biological effect is obtained by the physical and/or mechanical constraint applied on the tumor cells, said constraint resulting from the constraint field, itself resulting from the application of the gradient of magnetic field onto nanoparticles distributed in the neoangiogenic network surrounding the tumor.

In one embodiment the invention relates to a medical system comprising (1) injectable magnetizable nanoparticles and means for injecting the same, and (2) means for applying a physical and/or mechanical constraint to a tumor associated to a neoangiogenic network where, after having been injected, the particles are retained, said means for applying a physical and/or mechanical constraint being a generator releasing a gradient of magnetic field; and
wherein
the system is neither a cell construct nor an implant;
the system is not used for treating a tumor by pharmaceutical means such as drug targeting or thermotherapy;
the particles are not used such as drug carrier or as imaging agent.

In one embodiment, this invention also relates to a method of treatment which is performed via the constraint applied on the cells; this constraint is a mechanical constraint. In one embodiment, this invention relates to a method of treatment which is performed via the constraint applied on the cells; this constraint is a contact-free constraint. The original approach of this invention shows that the mechanical constraint results from the force applied locally by the nanoparticles situated within the tumor region. The gradient of magnetic field directs the constraint field to the interior of the sphere, i.e. to the tumor cells. In the present invention, no movement of the particles is observed.

In particular, the invention relates to a method for treating tumors by physical and/or mechanical means.

In one embodiment, the method of the invention further comprises a pharmaceutical agent. In one embodiment, the method of the invention does not comprise a pharmaceutical agent. In one embodiment, the method of the invention is not a pharmaceutical method.

DEFINITIONS

In the present invention, the following terms have the following meanings:
"About" refers preceding a figure means plus or less 10% of the value of said figure.
"Phenotype" refers to the observable properties (structural and functional) of a living organism. In cancerology, the cell or tissue phenotype of a malignant tumor is observable properties which are disturbed, with comparison to the corresponding normal cell or tissue. For cell phenotype, said observable properties may be, none limitatively, growth, cell division, apoptosis, cell death, migration ability etc.
"Neoangiogenic network" refers to the new vessels developing in the proximal area of the tumor. Proangiogenic molecules released from tumor cells are able to induce new vessel formation.
"Gradient": a gradient is a vector indicating the variation or change, in space, of a physical quantity. In the meaning of this invention, a gradient of magnetic field is the rate of change of the strength of the field over distance. Magnetic field gradients are the forces used in quantum physics that exert a translational force on both a stationary and moving magnetizable particles. This is in contrast to a uniform magnetic field such as from a bipolar magnet which exerts zero force on magnetizable particles. The force/gradient relationship is represented by the formula $F=\nabla P$ wherein F is the force, $\nabla$ is the gradient as a vector quantity and P is the magnetic potential. The gradient is measured in T/mm.

"Constraint field" is a field applying a mechanical force.

"Constraint" refers to a force divided by a surface, therefore homogeneous to a pressure and measured in Pascal (Pa); the state of stress or internal forces involved in different parts of the solid is defined by a stress tensor (Cauchy, 1822). These efforts are defined at each point of the solid and referred to as stress field or more generally tensor field. In physics of continuous medium, a field is, for each point of space-time, the value of a physical quantity. This quantity may be scalar (pressure) vector (magnetic field) or tensor.

"Malignant tumor" refers to a cancerous tumor.

"Mechanical" refers to a physical action on an object or a subject; in particular it refers to the propagation of a physical signal in a material environment transmitted to an object or a subject.

"Nanoparticle" refers to nanospheres having a spherical shape, and a diameter ranging from 0.1 to 1000 nanometers. According to this invention, the nanoparticles are not hollow spheres, but solid spheres.

"Particle" refers to magnetic beads under the form of unitary nanoparticles or of multitude of nanoparticles; said particle having a diameter ranging from 0.1 to 1000 nanometers; preferably the diameter is higher than 100 nm.

"Physical means" refers to non-chemical means.

"Stroma" refers to the tissue which forms the structure of an organ.

"Tumor region" refers to a tumor; the extracellular matrix and/or the stroma; and the peripheric network of neovessels (the neoangiogenic network) surrounding the tumor.

"Tissue" refers to a consistent assembly of cells presenting the same phenotype.

BRIEF DESCRIPTION OF THE DRAWINGS

FIG. 3 also shows the limitation of the growth of the cancer cells after experimentation, with comparison to control.

LIST OF REFERENCES

Figure 1:
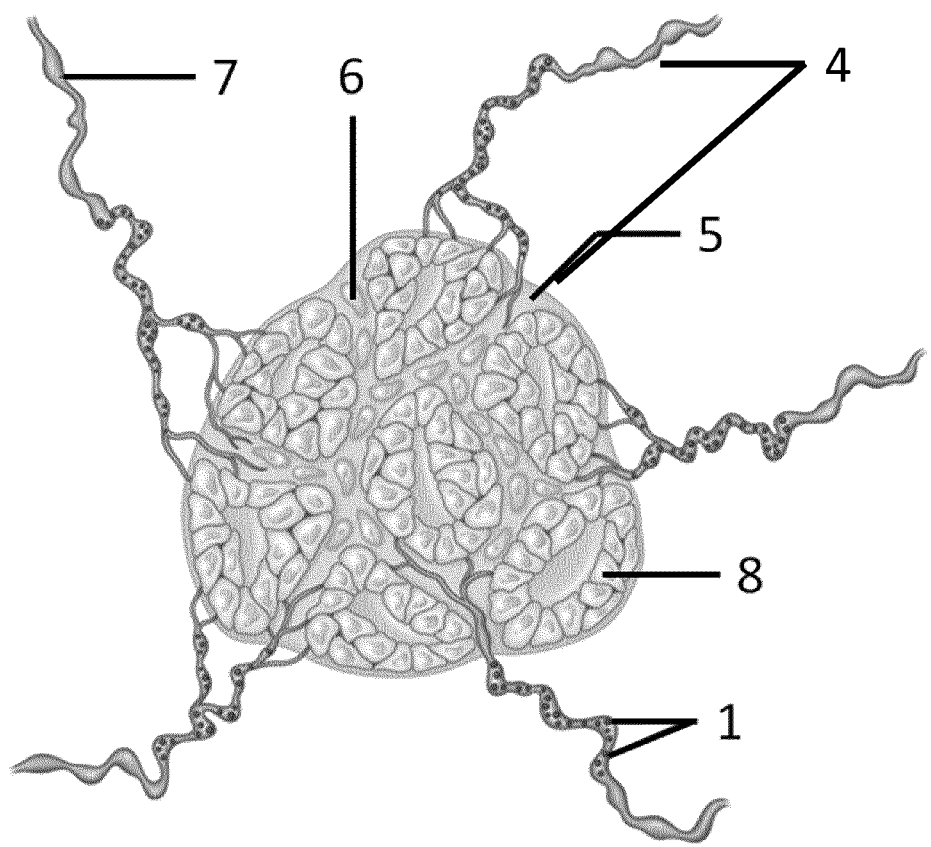
FIG. 1 illustrates the general principle of the invention on a tumor.

1—Particles or nanoparticles
2—Gradient of magnetic field
3—Collagen
4—Neoangiogenic network
5—Stroma
6—Tumor cells
7—Neovessels
8—Cancer cells
9—Magnet
10—Mouse grafted
11—Increase of the active part of the tumor on the West side
12—Decrease of the active part of the tumor on the muscle side
13—Necrosis
14—Living part of the tumor subcutaneously grafted
15—Muscle
16—Skin

DETAILED DESCRIPTION

This invention relates to a medical system comprising (i) an injection device comprising injectable magnetizable nanoparticles 1 and means for injecting the same, and (ii) means for applying a physical and/or mechanical constraint to a tumor associated to a neoangiogenic network 7 where, after having been injected, the particles 1 are retained.

By definition, it is understood by a neoangiogenic network, new blood vessels developing in the proximal area of the tumor while the stroma refers to the tissue which forms the structure of an organ. The stroma does not represent a vascularization network. Thus, the stroma is not a neoangiogenic network.

Consequently, the present invention relates to a medical system for treating by physical and/or mechanical means tumor cells, wherein said means comprise magnetic particles specifically retained in the neoangiogenic network.

In one embodiment, the medical system is not a cell construct or an implant.

In one embodiment, the medical system does not comprise a pharmaceutical agent for treating the tumor; in particular the nanoparticles are not used as drug carriers.

In one embodiment, the medical system is not for use as an imaging or a contrast system.

Tumor

In one embodiment, the tumor is associated with an angiogenic network 7. In another embodiment, the tumor is a locally advanced tumor. In one embodiment, the tumor is a malignant epithelial tumor. In one embodiment, the malignant tumor is pancreas cancer. In one embodiment, the malignant tumor is liver cancer. In another embodiment, the malignant tumor is breast cancer. In one embodiment, the tumor is within an animal or a human body.

Means for Applying a Mechanical and/or Physical Constraint

In one embodiment, the means for applying a mechanical and/or physical constraint is a generator releasing a gradient of magnetic field 2. In one embodiment, the magnetic field generator is controlled to produce a gradient of magnetic field 2. In on embodiment, the generator comprises an electromagnet 9. In another embodiment, the generator is a coil, preferably a moving coil, more preferably a Helmotz coil in a tumble configuration.

In one embodiment, the means for applying a mechanical and/or physical constraint further comprise at least one magnet, permanent magnet and/or electromagnet; preferably said means further comprise more than one external magnet, permanent magnet and/or electromagnet; more preferably more than one external magnet, permanent magnet and/or electromagnet are localized at various preferably opposite sides of the tumor.

In a very preferred embodiment, means for applying a mechanical and/or physical constraint (such as for example external magnets) are located outside the tumor, preferably located outside the body of the subject. In one embodiment, the means are moving, preferably turning around the tumor region. In one embodiment, the means are located at a distance at the tumor ranging from 0.1 to 100 mm; preferably 1 to 10 mm.

In one embodiment, the magnetic field is a variable or constant external field, having a frequency varying or ranging from 0.1 Hz to 1 TeraHz, preferably from 1 Hz to 1 MHz, more preferably from 10 Hz to 500 kHz.

In one embodiment, the magnetic field ranges from 0.1 µT to 50 T, preferably from 0.01 mT to 5 T, more preferably from 0.1 mT to 700 mT.

In one embodiment, the magnetic field is moving, preferably turning around the tumor region.

In one embodiment, the magnetic field is not an alternative field. In one embodiment, the magnetic field is not an alternative current electric field.

In one embodiment, the gradient of magnetic field 2 varies in intensity, frequency and/or in direction. Advantageously, the gradient of magnetic field 2 is applied in a way such that the constraint on the tumor varies in intensity, direction and frequency. One skilled in the art shall modify the intensity, frequency and/or in direction of the gradient of magnetic field, depending on the location of the tumor and its size and possibly on other biological data.

In one embodiment, the gradient of magnetic field 2 ranges from 0.001 to 10 T/cm, preferably from 0.01 to 1 T/cm, more preferably from 0.1 to 0.5 T/cm; even more preferably around 0.4 T/cm.

In one embodiment, the frequencies of the gradient of field 2 may be varied to search and reach a constraint field having the resonance frequency, or harmonics thereof, of the cytoskeleton and/or of cells walls and/or of the surrounding soft and/or hard tissues. Advantageously, the frequency of the gradient of field may be adapted so that the constraint field triggers the resonance frequency of the continuous assembly formed by the tumor cells components in the tumor.

In one embodiment, the system comprises means to vary the direction of the magnetic field or the direction of the generator, in order to direct the field.

Magnetizable Nanoparticles

In one embodiment, the particles or nanoparticles 1 comprises, are composed of or consists of any magnetizable material, preferably, iron oxide or manganese, more preferably magnetite ($Fe_3O_4$), maghemite ([gamma]-$Fe_2O_3$) or ferumoxides, i.e. a dextran-coated colloidal iron oxide, or mixtures thereof.

By particle, it is understood in the present invention, one unitary particle or an assembly of nanoparticles.

In one embodiment, the particles or nanoparticles 1 have a size or a hydrodynamic volume such that they cannot be uptaken by the tumor cells.

In one embodiment, the particles or nanoparticles 1 have a size or a hydrodynamic volume such that they are retained by the neoangiogenic network 7 surrounding the tumor and remain at the periphery of the tumor without entering into the tumor or the tumor cells.

In one embodiment, the particles or nanoparticles 1 have a mean diameter ranging from 30 to 1000 nm, preferably 40 to 800 nm, more preferably 60 to 300 nm.

In a very preferred embodiment, the particles or nanoparticles have a mean diameter higher than 100 nm in order to avoid capture by the cell tumors and/or organs; preferably about 200 nm.

In one embodiment, the quantity of the particles or nanoparticles 1 loaded in the body is ranging from 0.1 mg to 1000 mg, preferably 1 to 10, more preferably about 5 mg.

In one embodiment, the particles or nanoparticles 1 are not coated.

In one embodiment, the particles or nanoparticles 1 are coated with a non-pharmaceutical composition, preferably said nanoparticles 1 are coated with a hydrophilic coating, more preferably dextran.

In another embodiment, the particles or nanoparticles 1 are coated with a pharmaceutical composition.

In another embodiment, the particles or nanoparticles 1 are coated with at least one biochemical agent; preferably a peptide; more preferably, arginylglycylaspartic acid (RGD).

In another embodiment, the particles or nanoparticles 1 may be helped in their migration towards the tumor region, for example through specific coatings applied onto the nanoparticles 1 prior to injection.

In one embodiment, the particles or nanoparticles 1 are formulated within a suspension, wherein the particles or nanoparticles 1 are suspended in a colloidal or non-colloidal vehicle. In this embodiment, the injection device encompassed in this invention comprises a suspension comprising the magnetizable particles or nanoparticles 1 as described above.

In one embodiment, the particles or nanoparticles 1 are formulated within an emulsion, wherein the particles or nanoparticles 1 are in an emulsion. In this embodiment, the injection device encompassed in this invention comprises an emulsion comprising the magnetizable particles or nanoparticles 1 as described above.

This invention also relates to method for treating tumors by physical and/or mechanical means, especially tumors associated with a neoangiogenic network 7, comprising the steps of:

injecting a composition, preferably a suspension or an emulsion, containing the particles or nanoparticles 1, preferably magnetizable particles or nanoparticles, more preferably iron-based or ferric particles or nanoparticles having a mean diameter ranging from 30 to 1000 nm, preferably 40 to 800 nm, more preferably 60 to 300 nm;

optionally performing imaging using an imaging device to detect a concentration of particles or nanoparticles retained in the neoangiogenic network 7; and applying physical and/or mechanical means for applying a contact-free constraint onto a tumor in vivo, said physical and/or mechanical means being a gradient of magnetic field 2 and the application being directed to the tumor region.

The nanoparticles 1 used in the method of the invention are as described above. According to the invention, at least 25-60% of the injected particles or nanoparticles 1 are retained in the tumor neoangiogenic network 7. Without willing to be linked by a theory, the Applicant tends to believe that the particles or nanoparticles 1 of the system of the invention, when injected, benefit from the well-known Enhanced Permeability and Retention (EPR) effect, and preferably mainly from the enhanced retention effect, with regard to the neoangiogenic network 7. The EPR effect is the property by which certain sizes of particles or nanoparticles 1 tend to accumulate in tumor regions much more than they do in normal tissues. The EPR effect helps directing the particles or nanoparticles 1 to the tumor region. However, due to the nature and the size of the particles 1 of the invention, they may not enter or contact the tumor cells, and get retained in the neoangiogenic network 7 surrounding the tumor.

In one embodiment, the EPR ratio of the particles or nanoparticles 1 of the invention, i.e. the amount of injected particles or nanoparticles 1 reaching the neoangiogenic network 7 ranges from 25% to 60%. In another embodiment, the EPR ratio ranges from 30% to 40% of the injected particles 1. The EPR ratio may vary, depending on the size of the particles or nanoparticles 1 and/or the location of the tumor region and/or the histological nature of the tumor.

The particles or nanoparticles 1 are retained by the neoangiogenic network 7 surrounding the tumor; in one embodiment, the distribution of the particles or nanoparticles 1 forms a hollow and discontinuous sphere.

According to the invention, the particles or nanoparticles are not retained by or in the stroma.

According to the invention, the particles or nanoparticles 1 may not contact the tumor cells. In one embodiment, the distance between a tumor cell and the particles or nanoparticle 1 is at least 1 (one) micron, preferably 5 to 100 μnm.

In one embodiment, the amount of injected particles or nanoparticles 1 ranges from 100 μg to 10 g, preferably from 500 μg to 2 g.

The means for applying a contact-free constraint is an external generator as described above. By external is meant that the generation of the gradient of magnetic field 2 is located outside the tumor, preferably located outside the body of the subject. In one embodiment, the gradient of magnetic field 2 is applied for a period of time, ranging from 1 minute to 48 hours, preferably 15 minutes to 5 hours, this period of time being repeated over several weeks.

In one embodiment, the subject is an animal, including a human. The subject may be a male or a female. This subject encompasses, within his/her/its body a tumor associated with an angiogenic network 7. In one embodiment, the tumor is a locally advanced tumor. In one embodiment, the tumor is a malignant epithelial tumor. In one embodiment, the malignant tumor is pancreas cancer tumor. In another embodiment, the malignant tumor is breast cancer tumor.

This invention also relates to a method for modifying the cancerous phenotype of cancer cells to normal cells in a target region, the method comprising the steps of:
 injecting a composition, preferably a suspension or an emulsion, containing the particles or nanoparticles 1 as described above, such that the particles or nanoparticles 1 are retained by the neoangiogenic network 7 surrounding the tumor; preferably, the injection is performed intravenously and the particles or nanoparticles 1 migrate spontaneously to the neoangiogenic network 7 of the tumor;
 optionally performing imaging using an imaging device to detect a concentration of particles or nanoparticles 1 retained into the neoangiogenic network 7 at the periphery of the tumor; and
 implementing physical and/or mechanical means for applying a contact-free constraint, such as for example a contact-free pressure, onto the tumor cells, this means comprising or consisting of a gradient of magnetic field 2 applied on the particles or nanoparticles 1, in vivo, from an outside source of gradient of magnetic field 2.

In particular, the invention also relates to a method for reducing the volume and the surfaces of tumor cells in a target region, the method comprising the steps of:
 injecting a composition, preferably a suspension or an emulsion, containing the particles or nanoparticles 1 as described above, such that the particles or nanoparticles 1 are retained by the neoangiogenic network 7 surrounding the tumor; preferably, the injection is performed intravenously and the particles or nanoparticles 1 migrate spontaneously to the neoangiogenic network 7 of the tumor;
 optionally performing imaging using an imaging device to detect a concentration of nanoparticles 1 retained into the neoangiogenic network 7 at the periphery of the tumor; and
 implementing physical and/or mechanical means for applying a contact-free constraint, such as for example a contact-free pressure, onto the tumor cells, this means comprising or consisting of a gradient of magnetic field 2 applied on the particles or nanoparticles 1, in vivo, from an outside source of gradient of magnetic field 2.

EXAMPLES

The present invention is further illustrated by the following examples.

FIG. 1 illustrates a tumor encompassing, in its peripheric neoangiogenic networks 7, the nanoparticles 1 as described herein.

Figure 2:
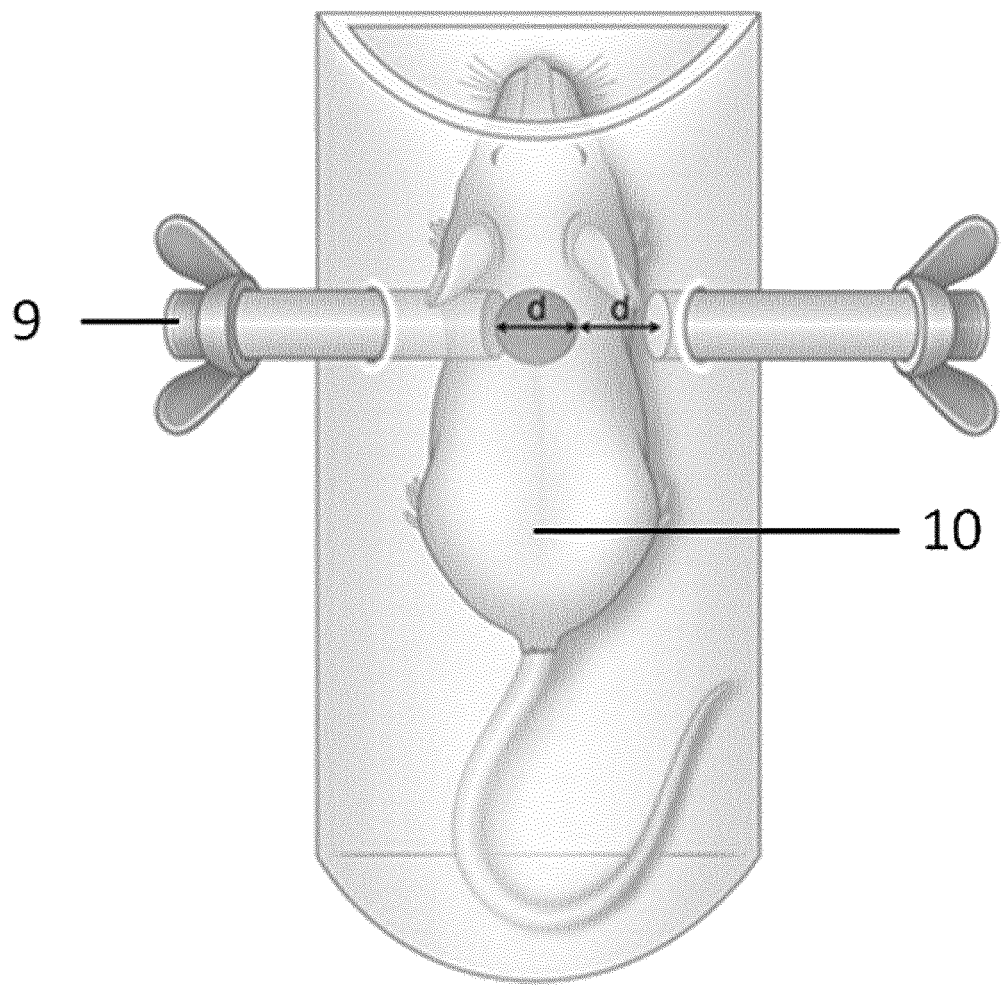
FIG. 2 is a scheme showing a nude mouse 10 grafted subcutaneously 14 with a mixture of ferric nanoparticles 1 and MDA MB 231 (origin: human breast cancer) cells.

In FIG. 2, the nude mouse 10 is grafted subcutaneously 14 with a mixture of ferric nanoparticles 1 and MDA MB 231 (origin: human breast cancer) cells. The mouse 10 is placed in the gap of two magnets 9, as shown on FIG. 2; in the example of FIG. 2, one magnet is as close as possible to the tumor, whereas the opposite magnet is at a distance d of the periphery of the tumor, this distance d corresponding to the diameter of the tumor.

Example 1: Feasibility Study

Objectives

The aims of the study were to analyze 10 human tumors (MDA-MB-231, breast cancer cell line), subcutaneously grafted in mice, and investigate:
 Microscopic features of subcutaneously grafted tumors (HES staining)
 Tumor cells iron accumulation (HES staining/Perls special stain)

Summary

Five mice 10 were subcutaneously grafted between skin (West side) 16 and muscle (East side) 15 with human cells of cell line MDA MB 231 (two xenografts per mouse). At the end of the study, all tumors were collected, fixed in 4% formalin and included in paraffin. One of the two xenografts from each mouse 10 was processed for evaluating histopathological features of the tumors (HES staining). Both xenografts samples from each mouse were processed for evaluating tumor cells iron accumulation (Perls special stain). In this study, the ten evaluated MDA-MB-231 xenografts presented comparable histological features, and appeared as undifferentiated carcinomas. Necrotic areas 13 were seen in the central parts of every tumor. They varied from 60% to 80% of the tumor surface. Iron deposits were located in the peri-tumoral areas. They appeared as brown granular deposits on HES stained slides and as dark blue granular deposits in Perls stained slides. No iron deposits were identified in tumor cells, in any tumor of any group.

Minimal deposits were observed in the cytoplasm of macrophages, and the necrotic areas 13.

Results

Tumor Histopathology (HES Staining)

Tumor microscopic features were evaluated on HES stained slides.

In this study, the evaluated MDA-MB-231 xenografts presented comparable histological features, and appeared as undifferentiated carcinomas, without glandular differentiation. These tumors were densely cellular, quite well demarcated and roughly nodular, with infiltrative growth in adjacent subcutaneous tissues, in particular nerves.

Quite numerous inflammatory cells were found in peri-tumoral fibrous stroma, as well as in adjacent tissues in smaller amounts (adipose tissue, skeletal muscle, skin). Those cells mostly consisted in pigment-laden macrophages, with some small lymphocytes and occasional granulocytes. Low numbers of similar inflammatory cells, including pigment-laden macrophages, were also observed in the scant intra-tumoral stroma. Those cells were mainly observed in peripheral parts of the tumor, probably spreading from the peri-tumoral stroma. Pigment-laden macrophages were medium to large-sized cells, and displayed a large cytoplasm which contained large amounts of brown granular pigment, often overlying and hiding round nuclei. Such pigment was occasionally found in the peri-tumoral and intra-tumoral stroma as granular pigment debris.

Tumor Cells Iron Accumulation (Perls Special Stain)

Perls' acid ferrocyanide reaction revealed iron compounds through dark blue labeling. For each tumor, three consecutive sections were evaluated. All three of those sections displayed comparable features.

No blue-stained iron deposits were identified in tumor cells, in any tumor of any group.

Conclusions

The particles 1 were distributed around the tumor and surprisingly formed a hollow and discontinuous sphere.

The conditions for applying a constraint on the tumor seem to be gathered.

Example 2: Ability to Modify the Cancerous Phenotype by a Constraint in Animals

Protocol

The aim of the study is to investigate the antitumor efficiency of nanoparticles activated by a magnetic field in the model of subcutaneous MDA-MB-231 human breast tumor bearing mice.

Test Substance

| Nanoparticles: | fluidMAG-D |
| Lot number: | 2202/12 |
| Storage condition: | +4° C. |
| Supplied quantity: | 100 mL (100 mg/mL) |

Treatment Doses—Route of Drug Administration

The amount of iron injected with cells is 5 mg. Nanoparticles are administered with tumor cells (at the time of tumor cells injection) to Balb/c Nude mice. The injection volume for the Nanoparticles is 300 μL/mouse/injection.

Animals

Forty five (45) female Balb/c Nude mice, 6-7 week-old and weighing 16-20 g at reception, were obtained from Charles River (France). Animals are observed for at least 7 days in a specific-pathogen-free (SPF) animal care unit before treatment. The animal care unit is authorized by the French ministries of Agriculture and Research (Agreement No. A21231011EA). Animal experiments are performed according to ethical guidelines of animal experimentation and the English guidelines for welfare of animals in experimental neoplasia. All procedures with animals are submitted to the Animal Care and Use Committee of Pharmacy and Medicine University (Dijon).

Submission of Animals to a Magnetic Field

When submitted to the magnetic field using magnet-bearing devices, animals are anaesthetized (with isoflurane) and body temperature of mice is maintained within physiological levels by infrared lamps.

When the tumors reached approximately one centimeter tumors in the treated group (i.e. Right Tumor G3, as explained hereafter), the mice 10 were placed in the gap of two magnets 9 in repulsive mode (see FIG. 2).

A gradient of magnetic field 2 is then applied. The gradient applied is about 0.4 Tesla/cm at a depth of 3 mm.

Cancer Cell Line

The cell line that is used is detailed in the table hereafter:

| Cell line | Type | Specie | Origin |
|---|---|---|---|
| MDA-MB-231 | Human breast adenocarcinoma | Human | ATCC |

Induction of MDA-MB-231 Tumors in Female Balb/c Nude Mice

Ten millions DA-MB-231 tumor cells resuspended in a volume of 0.3 mL RPMI 1640 medium containing 5 mg of nanoparticles or no nanoparticles are subcutaneously inoculated in the flanks of 45 female SWISS Nude mice, irradiated 24-72 hours before with a γ-source (whole body irradiation, 2 Gy, 60Co, BioMEP Sarl, Bretenière, France).

Tumors cells without the nanoparticles are injected in the left flank of all 45 mice.

Tumors cells with the nanoparticles are injected in the right flank of all 45 mice.

The day of tumor cells injection is considered as the day 0 (D0).

Treatment Schedule

The tumor volume is estimated by the formula:

$$\text{Tumor volume} = \frac{1}{2} \times \text{length} \times \text{width}^2$$

When the mean tumor volume reaches approximately 100-200 mm$^3$, 36 tumor bearing female Balb/c Nude mice are randomized into 3 groups (one group of 8 mice and two groups of 14 mice) according to their individual tumor volumes. The treatment schedule was chosen as follows:

Group 1: The tumor on the left flank (containing no nanoparticles) of the eight (8) mice is submitted to the magnetic field once a day for two consecutive hours for 21 consecutive days.

Group 2: The tumors on the left flank (containing no nanoparticles) and on the right flank (containing nanoparticles) of the fourteen (14) mice are not submitted to the magnetic field.

Group 3: The tumor on the right flank (containing nanoparticles) of the fourteen (14) mice is submitted to the magnetic field once a day for two consecutive hours for 21 consecutive days.

Treatments (i.e. submission to the magnetic field) start on the day after randomization. The table 1 below summarizes the treatment schedule:

TABLE 1

Treatment schedule for mice bearing subcutaneous MDA-MB-231 human breast tumor.

| Group | No. mice | Nanoparticles | | Submission to magnetic field | | Duration |
|---|---|---|---|---|---|---|
| | | Left tumor | Right tumor | Left tumor | Right tumor | |
| 1 | 8 | No | Yes | Yes | No | 2 hours, every day, 21 days |
| 2 | 14 | No | Yes | No | No | — |
| 3 | 14 | No | Yes | No | Yes | 2 hours, every day, 21 days |

Thus the treated group—group 3 right tumor—was compared with three control groups:
Group with nanoparticles 1, without gradient field 2: group 1 right tumor and group 2 right tumor.
Group without nanoparticles 1, with field gradient 2: group 1 left tumor.
Group without nanoparticles 1, without field gradient 2: group 2 left tumor and group 3 left tumor.

Tumor Samples Collection

Tumors are resected and cut into two pieces. The two pieces will be fixed in 10% neutral buffered formalin.

Results

Figure 3:
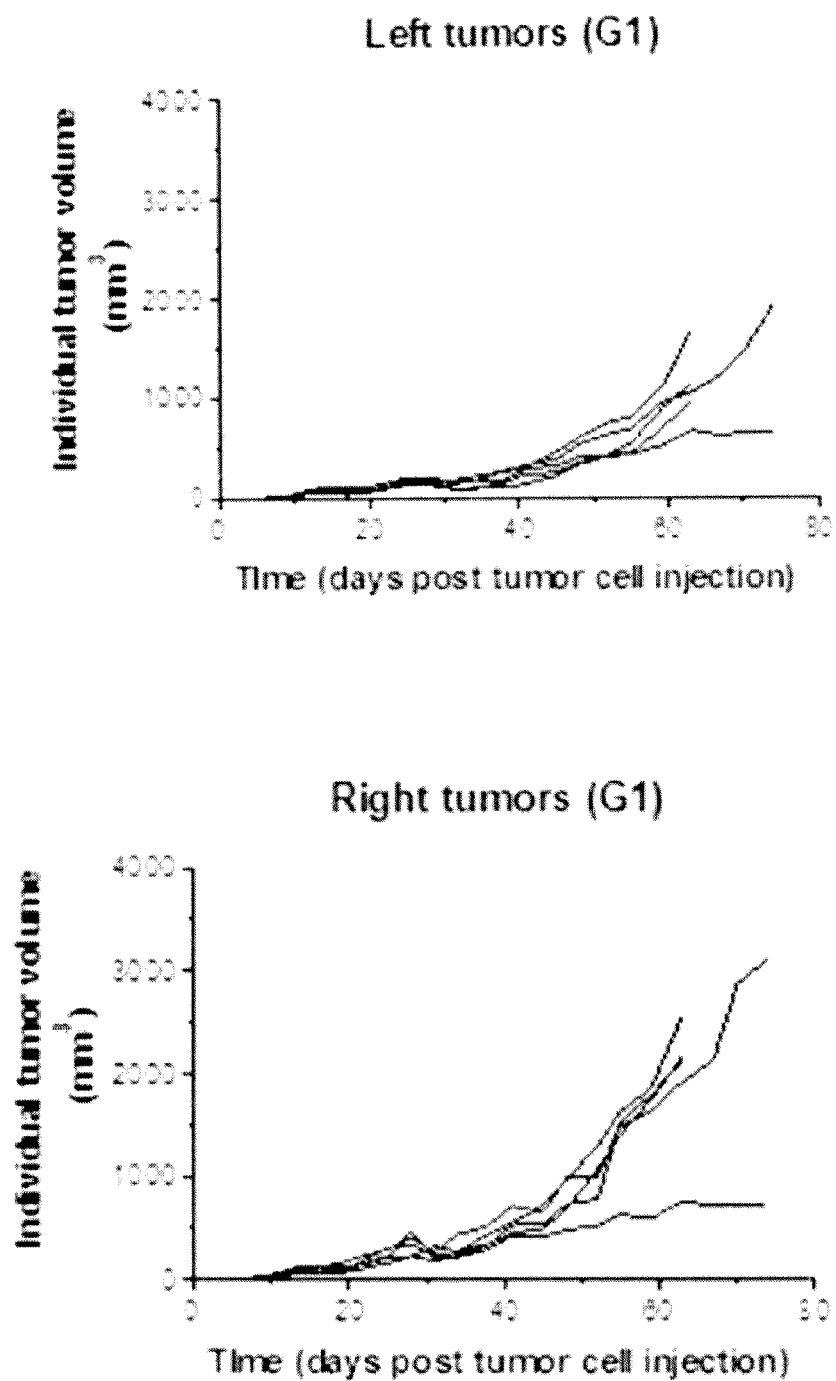
FIG. 3 illustrates the individual growth curves of the grafted tumors from D0 to D80.
Figure 3:
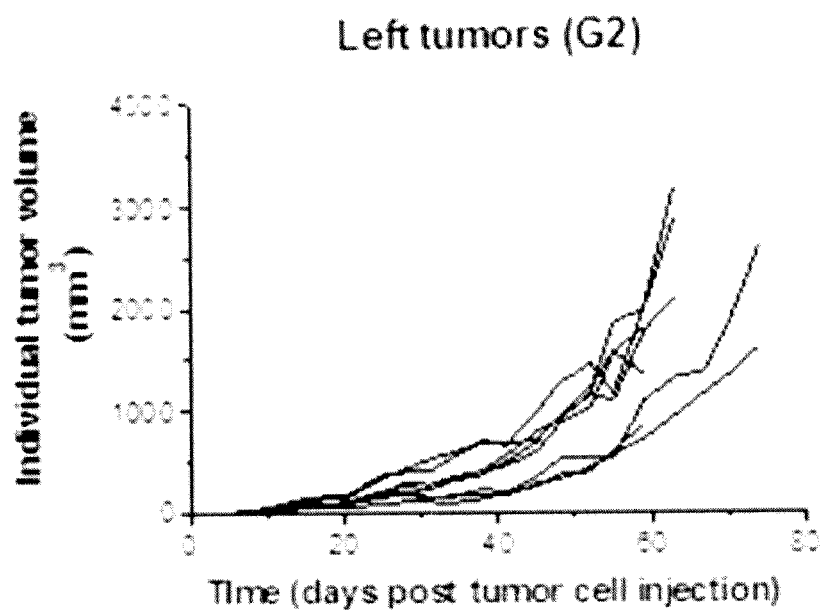
Figure 3:
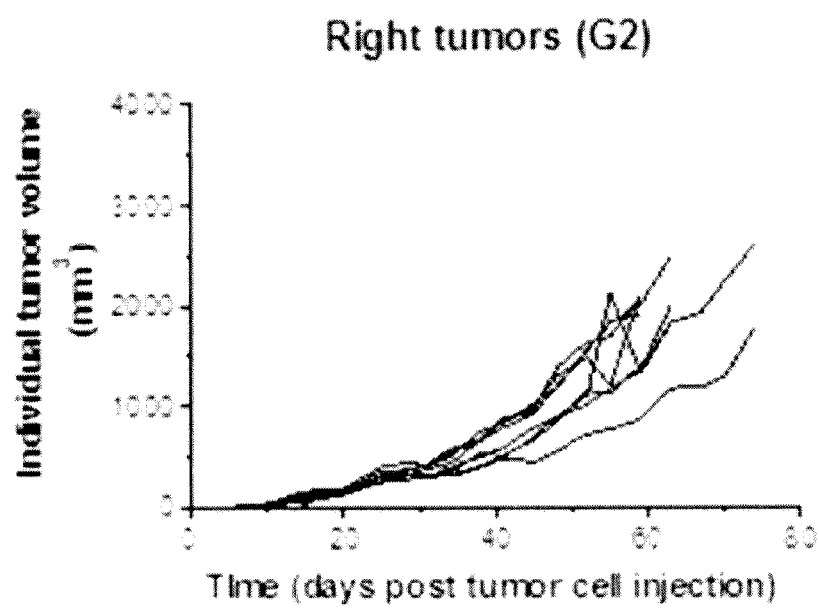
Figure 3:
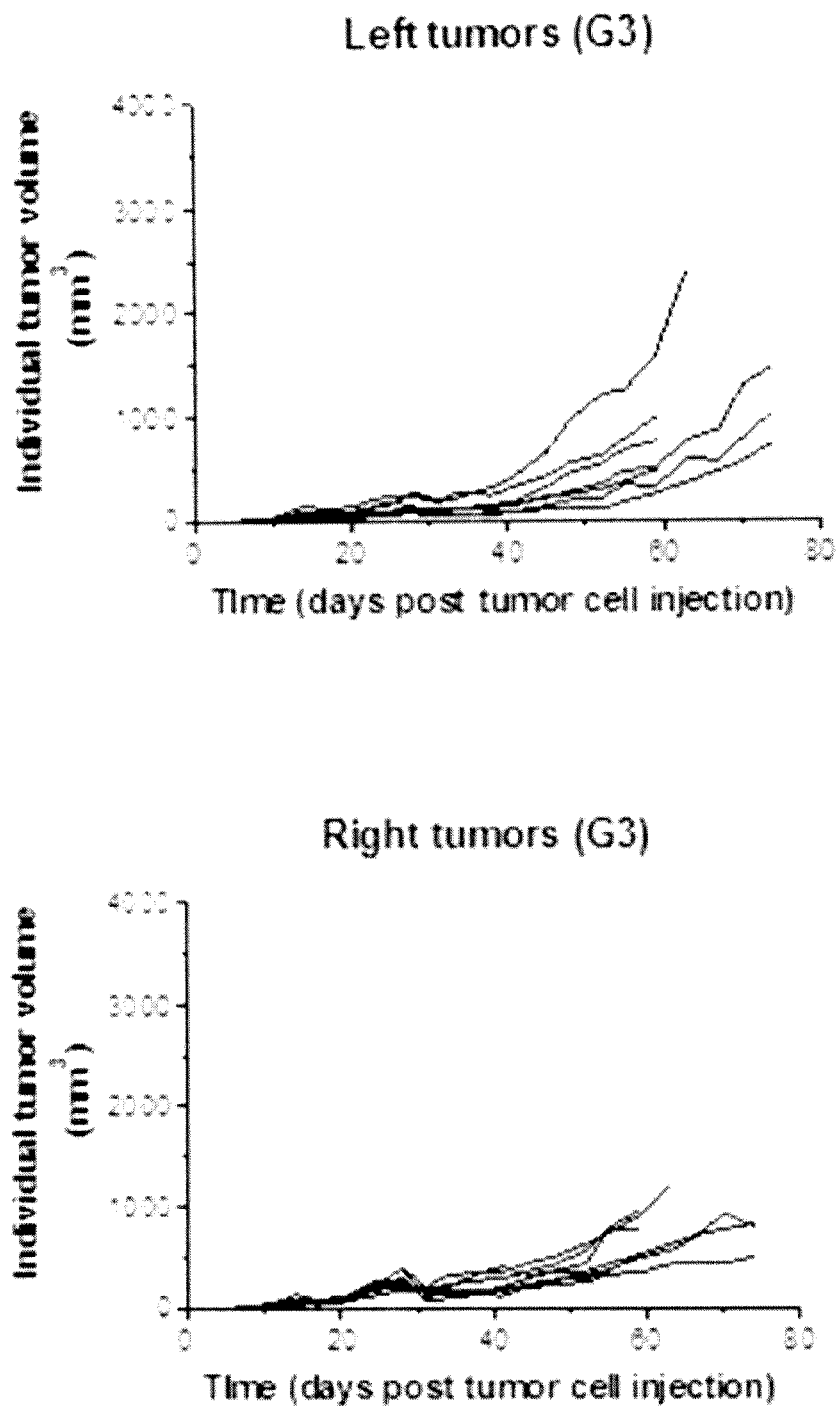

The treated group (with nanoparticles 1 and with gradient field 2, i.e. Right Tumor G3) was compared with three control groups: There were two statistically significant changes (p<0.05):

On the one hand the overall tumor growth 11/12 is lower in the treated group compared to the three control groups, see FIG. 3. The more detailed analysis of treated tumors was used to compare the West side and the East side: increase of the thickness of the active part of the tumor on the West side 11 and decrease of the active part of the tumor on the East side 12 in the treated tumors (with nanoparticles an gradient of magnetic field) when compared to the control groups.

On 59 days after graft (D59), the tumoral volume is much lower in the group Right Tumor G3 (7 mice), than all control groups (33 mice): the median in the treated group is 529.4 mm$^3$ whereas the median in the control group is 1334 mm$^3$ (p=0.014<0.05).

Figure 4A:
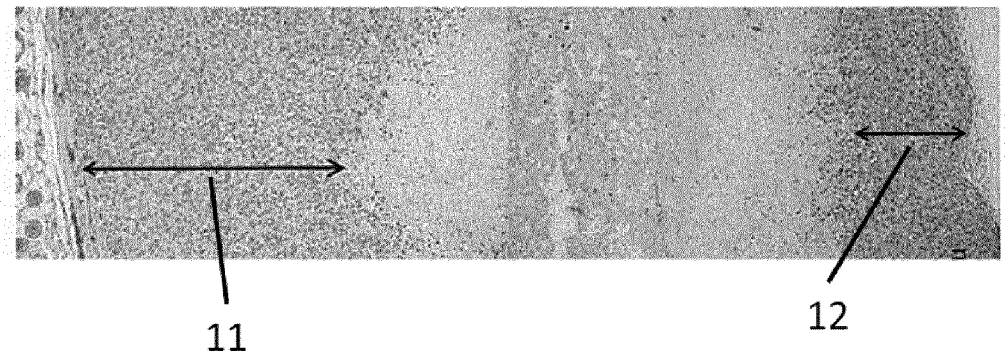
FIG. 4 shows the proof of concept, in photo 4A and scheme 4B.
Figure 4B:
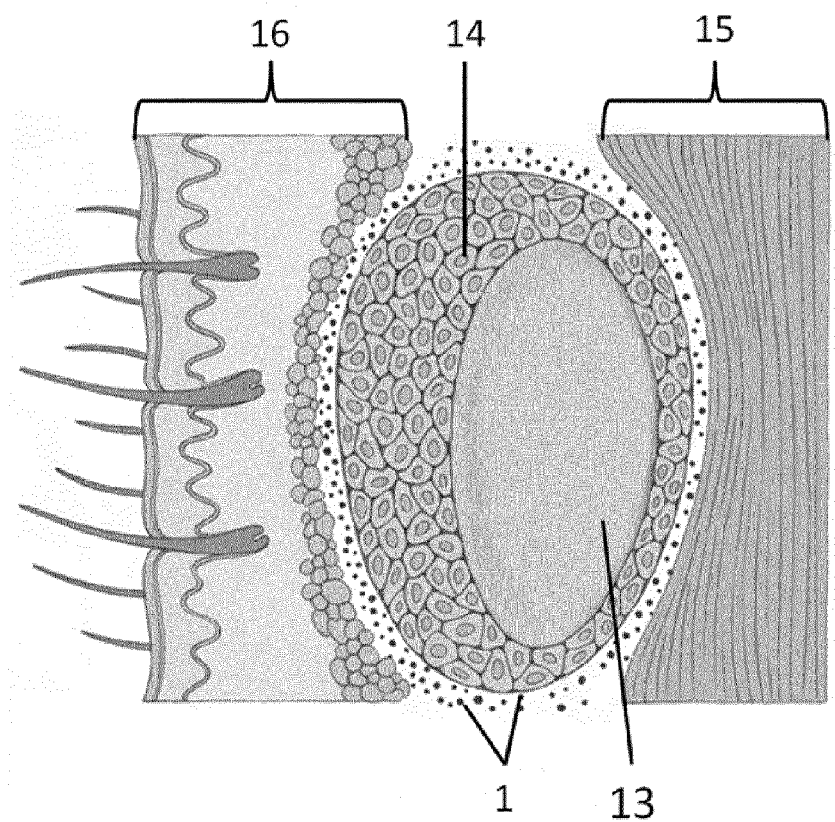
Figure 5:
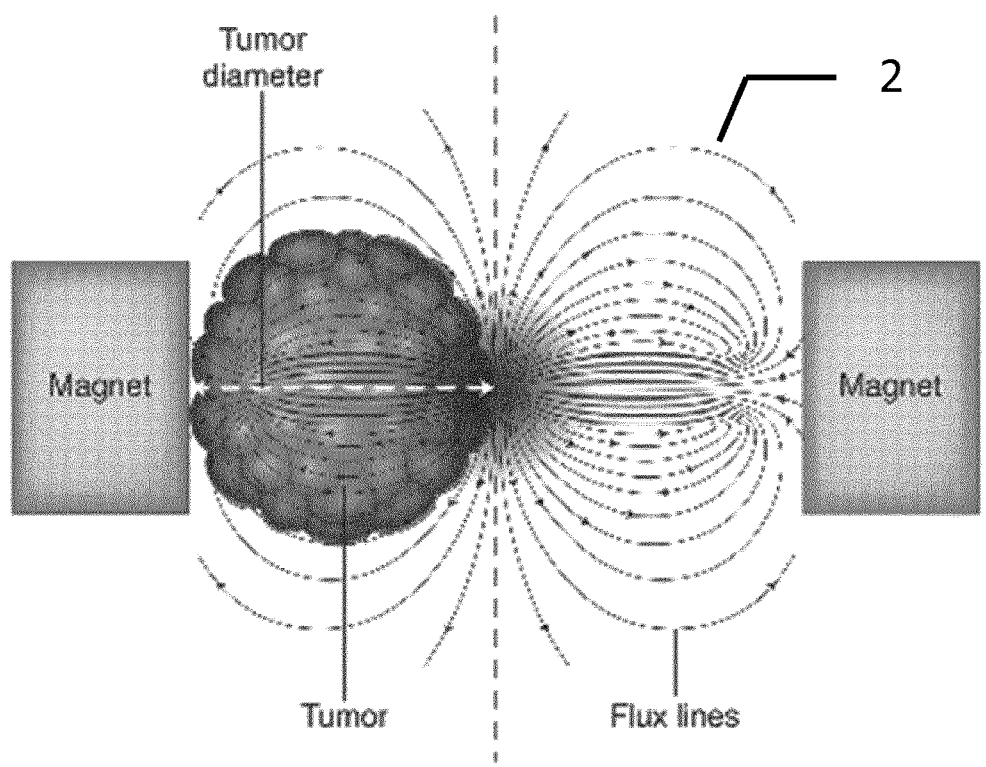
FIG. 5 is a scheme showing the positioning of two magnets on both sides of the tumor of a mouse.

The result on the tumor is shown in FIG. 4A and schematized in FIG. 5B.

To the Applicant's knowledge, it is the first evidence in vivo action of physical constraint generated by a gradient of magnetic field on tumor growth.

Example 3: Ability to Modify the Volume and Surfaces of a Tumor by a Physical and/or Mechanical Constraint in Animals Objectives The aim of the study is to investigate the reduction of the tumor volume and the surfaces due to nanoparticles activated by a gradient of magnetic field in the model of subcutaneous MDA-MB-231 human breast tumor bearing mice.

Summary

Mice were subcutaneously grafted between skin and muscle with human cells of cell line MDA MB 231. When tumors reached approximately one centimeter tumors in the treated group, the mice were placed in the air-gap of two magnets in a repulsive mode with a particular geometry as shown FIG. 2.

Experimental Groups 79 mice having a one-centimeter-sized tumor were distributed in 4 groups:

G1' (treated group): experiment wherein particles are injected in a mouse which is then put under a gradient of magnetic field.

G2' (control group): Experiment wherein particles are injected in a mouse but which is not put under a gradient of magnetic field.

G3' (control group): Experiment wherein a mouse is put under a gradient of magnetic field but no particle is injected into the mouse.

G4' (control group): Group wherein no particle is injected into mice and no gradient of magnetic field is used.

The day of tumor cells injection is considered as the day 0 (D0). The volume is calculated in mm$^3$.

Results

Tumor volume—In-vivo experiments

G1' Versus the Whole Untreated Group

Figure 8:
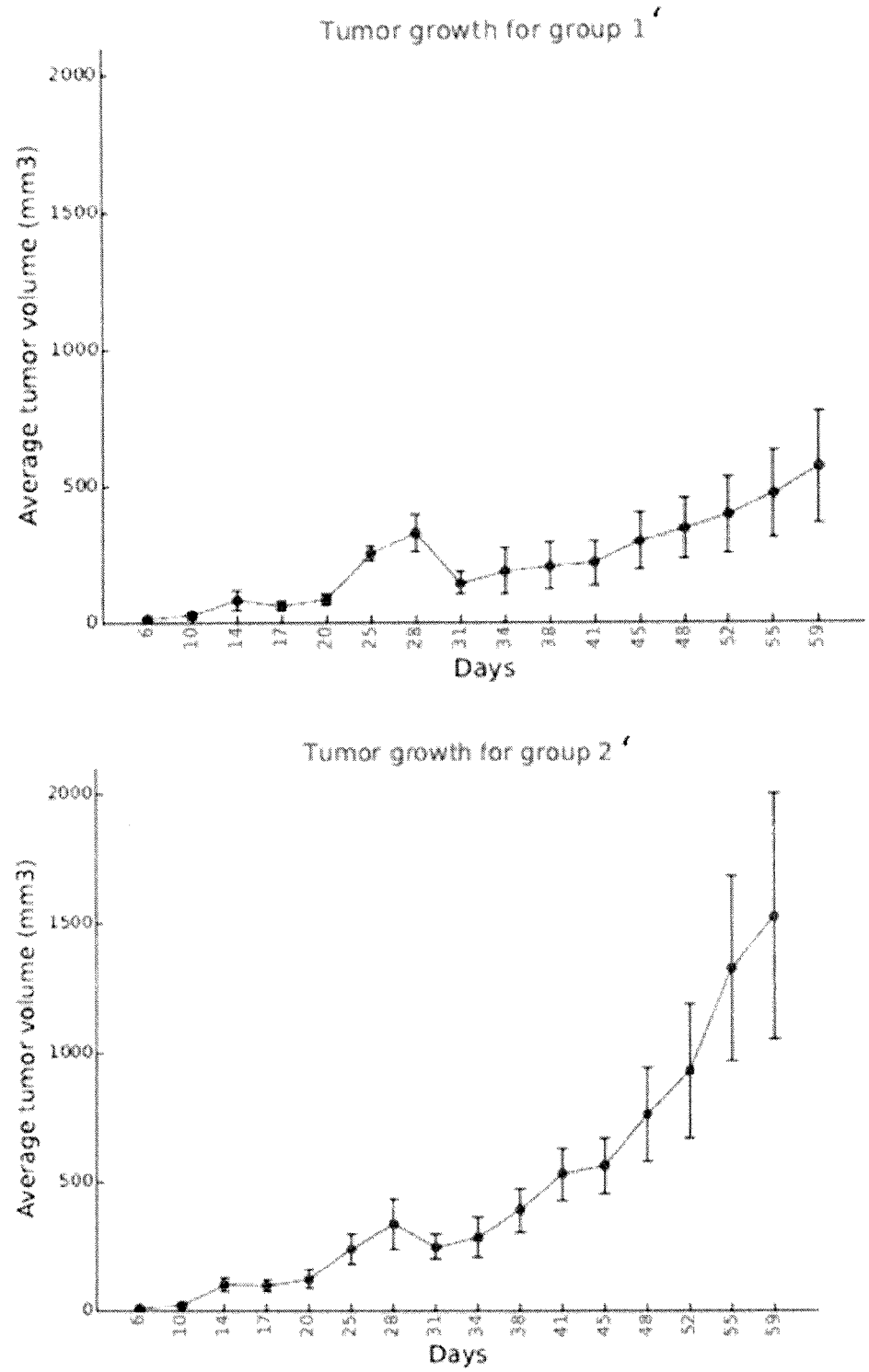
FIG. 8 shows the evolution of the average in vivo tumor volume for the treated group (G1') versus the control groups (G2'; G3' or G4').
Figure 8:
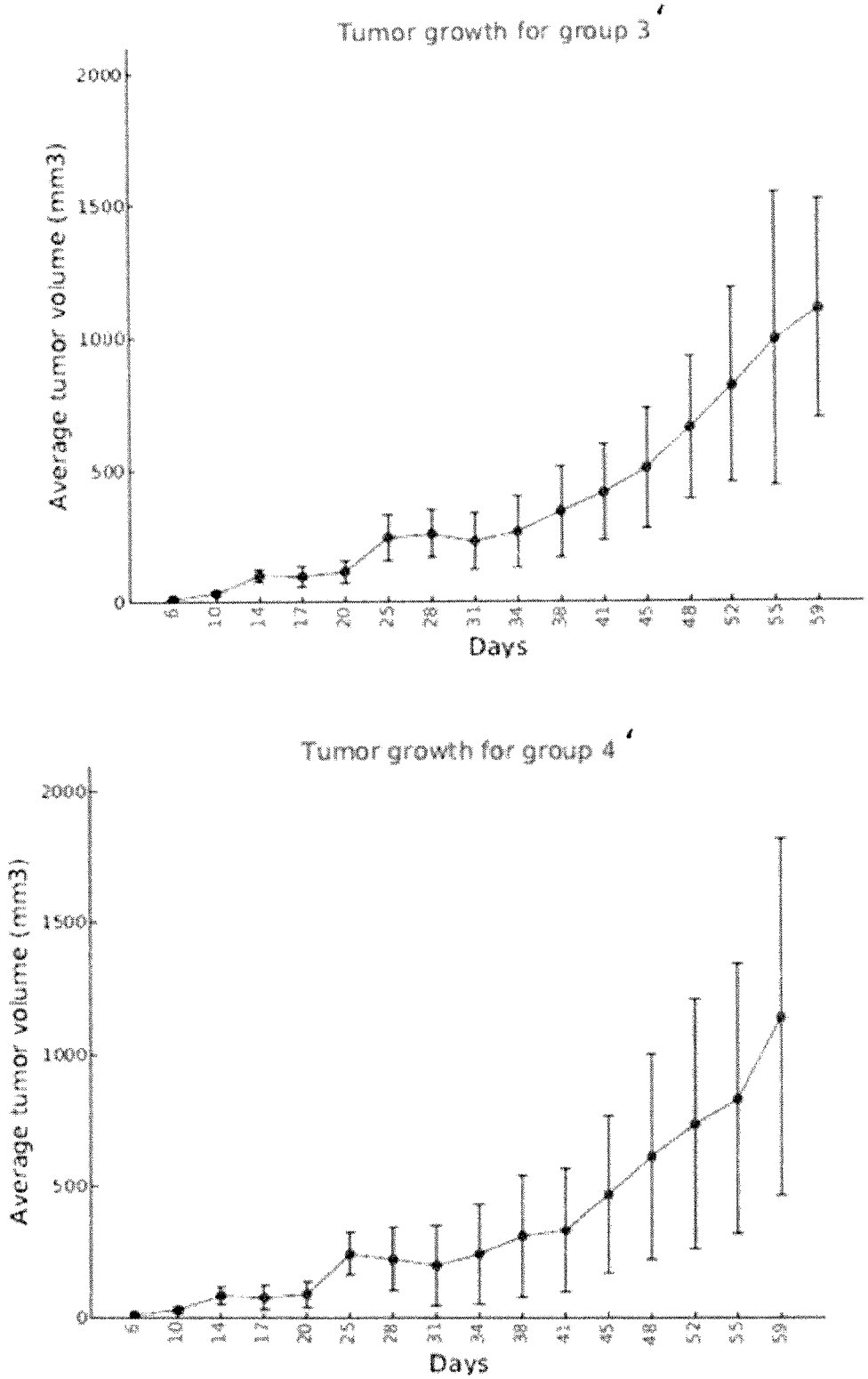

The treated group (G1') was compared to the whole untreated group comprising G2', G3' and G4'. The table 2 below and FIG. 8 summarize the results taken after 59 days for all the subcutaneously grafted mice.

TABLE 2

Statistical results for treated group (G1') of subcutaneously grafted mice versus to untreated groups (G2', G3' and G4').

| Group | Mean | Median |
|---|---|---|
| Treated (G1') | 646.5 | 529.4 |
| Untreated (G2', G3' and G4') | 1250 | 1334.0 | p-Values

The Wilcoxon test for comparing the median values between the treated group (G1') and the other groups (untreated) gives a p-value equal to 0.0146 (<0.05).

Thus, the treatment of breast tumor cells by magnetic particles under a gradient of magnetic field significantly reduces the tumor volume compared to the untreated groups (G2', G3' or G4').

G1' Versus Each Untreated Group

Figure 6:
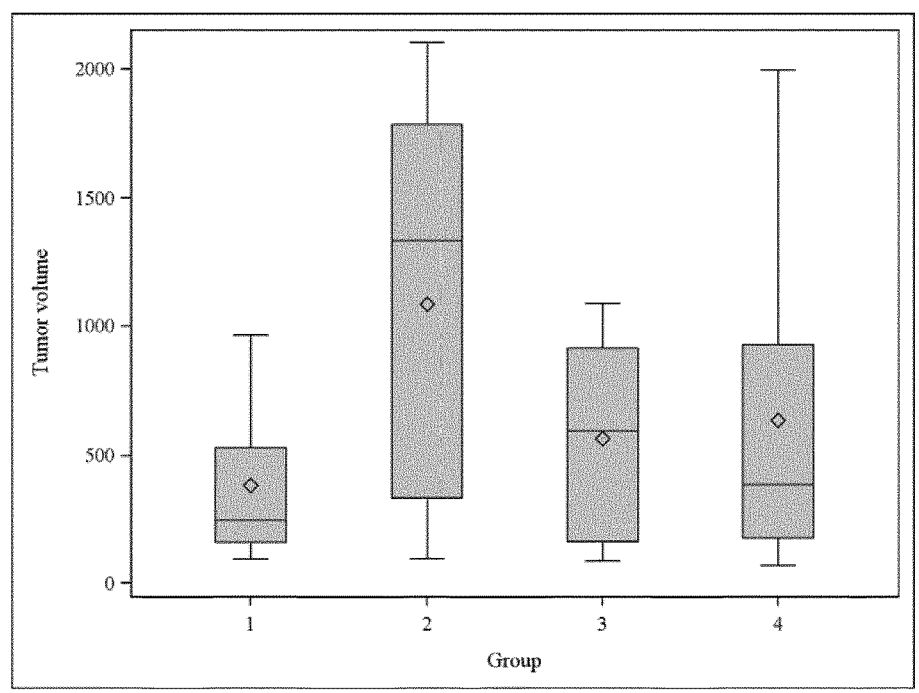
FIG. 6 shows the comparison of the tumor volume for all mice between the treated group (G1') to the three controls groups (G2'; G3' or G4').

Then, the treated group (G1') was compared to each untreated group (G2', G3' or G4'). The table 3 below and FIG. 6 summarize the results taken after 60 days for all the subcutaneously grafted mice of each group:

TABLE 3

Comparison of the tumor volume of treated group (G1') and each of the control group (G2', G3' or G4') after 59 days for all the subcutaneously grafted mice.

| Group | Mean | Median |
|---|---|---|
| 1' | 382.862 | 246.010 |
| 2' | 1085.634 | 1334.170 |
| 3' | 564.826 | 595.840 |
| 4' | 635.110 | 387.640 |

It appears that the treated group (G1') is the only group to provide the lower tumor volume.

Thus, this example shows that the medical system comprising injectable nanoparticles and a gradient of magnetic field is the best method to reduce a tumor volume by mechanical and/or physical means.

West and East surfaces—Ex-vivo experiments

Figure 7A:
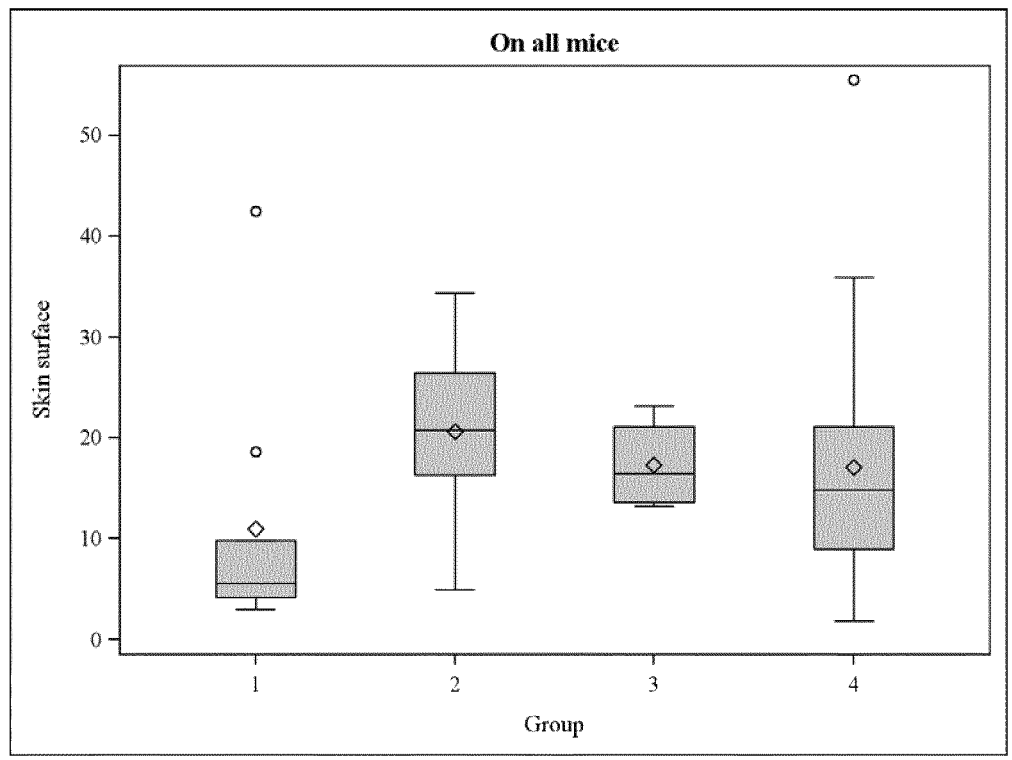
FIG. 7 shows the comparison of the histological surfaces for all mice of the West side (FIG. 7A) or the East side (FIG. 7B) of the tumor between the treated group (G1') to the three controls groups (G2'; G3' or G4').
Figure 7B:
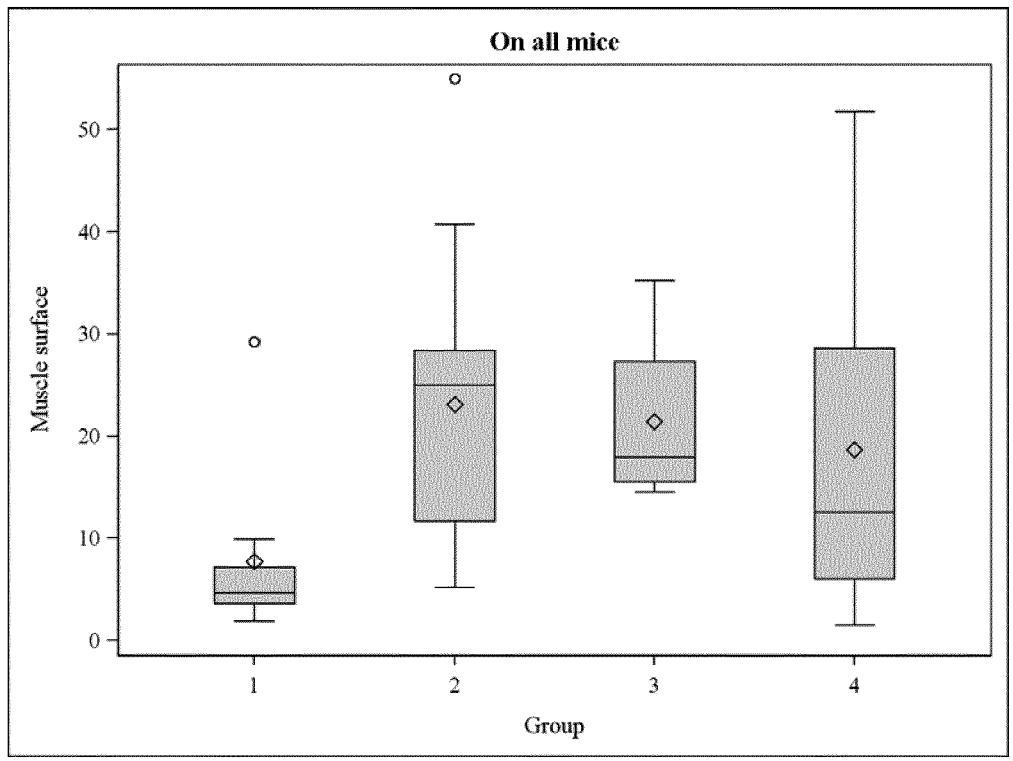

The finer analysis of tumors allowed comparing the West side and the East side. Total surface measurement is available for 51 tumors and the results are shown on Table 4 and FIG. 7.

TABLE 4

Comparison of West and East surfaces of treated group (G1') and the control groups (G2', G3' or G4') after 59 days for all the subcutaneously grafted mice.

| Variable | Group | Mean | Median |
|---|---|---|---|
| West surface | 1' | 10.937 | 5.582 |
|  | 2' | 20.594 | 20.795 |
|  | 3' | 17.320 | 16.456 |
|  | 4' | 17.084 | 14.784 |
| East surface | 1' | 7.727 | 4.714 |
|  | 2' | 23.108 | 24.993 |
|  | 3' | 21.431 | 17.952 |
|  | 4' | 18.650 | 12.521 | p-Values

A one-way analysis of variance for the West and East surface was performed with log-transformation on the group encompassing both the treated group (G1') and the control groups (G2'-G4'):

| Effect | Signification (p-value) |
|---|---|
| West surface - on all mice - Global Effect | |
| Group | Significant ($p = 0.021$) |
| East surface - on all mice - Global Effect | |
| Group | Significant ($p = 0.004$) |

These first results show that the group has a significant global effect both on the West and the East surface of the tumor.

p-Value Comparison Between Untreated Groups

The pairwise comparison using Tukey's adjustment between untreated groups (one-way analysis of variance) led to the results shown in Table 5.

TABLE 5 p-value comparison of the control groups (G2', G3' or G4') after 59 days for all the subcutaneously grafted mice.

| Comparison | Estimate | Signification (p-value) (Tukey's adjustment) |
|---|---|---|
| West surface - on all mice - Comparison untreated groups | | |
| G2' vs. G3' | 0.037 | Not Significant ($p = 0.973$) |
| G2' vs. G4' | 0.141 | Not Significant ($p = 0.372$) |
| G3' vs. G4' | 0.104 | Not Significant ($p = 0.799$) |
| East surface - on all mice - Comparison untreated groups | | |
| G2' vs. G3' | −0.028 | Not Significant ($p = 0.988$) |
| G2' vs. G4' | 0.159 | Not Significant ($p = 0.377$) |
| G3' vs. G4' | 0.187 | Not Significant ($p = 0.571$) |

All p-values are higher than 0.05, so there is no significant difference between the three groups untreated as expected.

p-Value Comparison Between the Treated Group (G1') and an Untreated Group

Finally, a mixed up of this 3 groups is realized and one-way analysis of variance is performed using contrast option shown in Table 6.

TABLE 6 p-value of the treated group (G1') compared to the untreated group comprising a part of G2', G3' and G4' after 59 days for all the subcutaneously grafted mice.

| Comparison | Estimate | Signification (p-value) (Tukey's adjustment) |
|---|---|---|
| West surface - on all mice - Comparison untreated groups | | |
| G1' vs ($\frac{1}{3}$ * G2' + $\frac{1}{3}$ * G3' + $\frac{1}{3}$ * G4') | −0.344 | Significant ($p = 0.005$) |
| East surface - on all mice - Comparison untreated groups | | |
| G1' vs ($\frac{1}{3}$ * G2' + $\frac{1}{3}$ * G3' + $\frac{1}{3}$ * G4') | −0.485 | Significant ($p = 0.001$) |

Surprisingly, the results show that the surfaces of the treated group are significantly different to untreated groups (mixed up). The surfaces on group treated are lower than on group untreated (estimate of difference is equal to −0.344 log for West side and to −0.485 for East side).

Conclusion

These results demonstrate that the Applicant has discovered a medical system allowing acting on the phenotype of tumor cells, reducing the tumor volume and the surfaces exposed to a mechanical and/or physical constraint implemented by injectable particles and an external gradient of magnetic field.

The invention claimed is:

1. A medical system comprising:
   injectable magnetizable nanoparticles having a mean diameter ranging from 10 to 800 nm;
   a device for injecting the nanoparticles; and
   a generator that releases a gradient of magnetic field for applying a mechanical constraint comprising contact-free compression, actuated by the injected nanoparticles, onto tumor cells of a tumor having a neoangiogenic network where, after having been injected, at least 25-60% of the injected nanoparticles are retained in the tumor neoangiogenic network to apply the contact-free compression onto the tumor cells,
   wherein the medical system is free of being a cell construct, free of being an implant, free of any pharmaceutical agent for treating the tumor, free of the nanoparticles being drug carriers, and free of the nanoparticles being imaging agents.

2. The medical system according to claim 1, wherein the nanoparticles are composed of iron oxide.

3. The medical system according to claim 2, wherein the nanoparticles comprise magnetite (Fe3O4), maghemite ([gamma]-Fe2O3), ferumoxides or mixtures thereof.

4. The medical system according to claim 2, wherein said nanoparticles are coated with a non-pharmaceutical composition.

5. The medical system according to claim 2, wherein said nanoparticles have a mean diameter ranging from 20 to 300 nm.

6. The medical system according to claim 2, wherein the nanoparticles are suspended in a colloidal or non-colloidal vehicle.

7. The medical system according to claim 1, wherein said nanoparticles are coated with a non-pharmaceutical composition.

8. The medical system according to claim 7, wherein said nanoparticles have a mean diameter ranging from 20 to 300 nm.

9. The medical system according to claim 7, wherein the nanoparticles are suspended in a colloidal or non-colloidal vehicle.

10. The medical system according to claim 1, wherein said nanoparticles have a mean diameter ranging from 20 to 300 nm.

11. The medical system according to claim 10, wherein the nanoparticles are suspended in a colloidal or non-colloidal vehicle.

12. The medical system according to claim 1, wherein the nanoparticles are suspended in a colloidal or non-colloidal vehicle.

13. The medical system according to claim 1, wherein the generator releases the gradient as a gradient of constant or variant magnetic field.

14. A method for treating a tumor region, said tumor region comprising a tumor, the extracellular matrix and/or the stroma and the neoangiogenic network surrounding the tumor, said method comprising the steps of:

injecting a composition containing an amount of nanoparticles, the nanoparticles having a mean diameter ranging from 10 to 800 nm; and using a generator for releasing a gradient of magnetic field to apply a contact-free mechanical constraint comprising contact-free compression, actuated by the injected nanoparticles, onto the tumor in vivo, wherein the nanoparticles are free of any pharmaceutical agent for treating the tumor by applying the contact-free compression onto the tumor cells.

15. The method according to claim 14, wherein the amount of injected nanoparticles ranges from 100 µg to 10 g.

16. The method according to claim 14, wherein at least 25-60% of the injected nanoparticles are retained in the tumor neoangiogenic network of the tumor region and the injected nanoparticles retained in the tumor neoangiogenic network apply the contact-free compression onto the tumor cells.

17. The method according to claim 14, wherein the tumor is a malignant epithelial tumor.

18. The method according to claim 14, wherein the tumor is a pancreas cancer tumor, or a breast cancer tumor.

19. A method for modifying the cancerous phenotype of cancer cells to normal cells in a tumor region, the method comprising the steps of:

injecting a composition containing nanoparticles such that the nanoparticles are retained by the neoangiogenic network of the tumor region, the nanoparticles being injectable magnetizable nanoparticles having a mean diameter ranging from 10 to 800 nm, the nanoparticles being free of any pharmaceutical agent for treating a tumor; and using a generator for releasing a gradient of magnetic field to apply a contact-free mechanical constraint comprising contact-free compression, actuated by the injected nanoparticles retained in the tumor neoangiogenic network, onto the cancer cells.

20. The method according to claim 19, wherein the modified cancer phenotype leads to the reduction of tumor volume and/or surfaces of the tumor cells.

* * * * *